United States Patent [19]

Milkowski et al.

[11] 4,243,585

[45] Jan. 6, 1981

[54] BENDODIAZOCINE DERIVATIVES AND PROCESS OF MAKING THE SAME

[75] Inventors: Wolfgang Milkowski, Burgdorf; Renke Budden, Peine; Siegfried Funke, Hanover; Rolf Hüschens, Hanover; Hans-Günther Liepmann, Hanover; Werner Stühmer, Eldagsen; Horst Zeugner, Hanover, all of Fed. Rep. of Germany

[73] Assignee: Kali-Chemie Aktiengesellschaft, Hanover, Fed. Rep. of Germany

[21] Appl. No.: 871,741

[22] Filed: Jan. 23, 1978

Related U.S. Application Data

[63] Continuation of Ser. No. 588,969, Jun. 20, 1975, abandoned, which is a continuation-in-part of Ser. No. 355,986, May 1, 1973, Pat. No. 3,998,809, Ser. No. 355,987, May 1, 1973, abandoned, and Ser. No. 355,989, May 1, 1973, abandoned.

[30] Foreign Application Priority Data

May 3, 1972 [DE] Fed. Rep. of Germany ....... 2221558

[51] Int. Cl.[3] ..................... A61K 31/55; C07D 245/06
[52] U.S. Cl. .......................... 260/239 BD; 564/133; 564/176; 564/166; 564/184; 424/244; 560/152; 560/170
[58] Field of Search ................................. 260/239 BD

[56] References Cited

U.S. PATENT DOCUMENTS

| 3,501,460 | 3/1970 | Kaegi ............................. 260/239 BD |
| 3,577,557 | 5/1971 | Ott ................................ 260/239 BD |
| 3,751,412 | 8/1973 | Natsugari et al. ............. 260/239 BD |
| 3,998,809 | 12/1976 | Milkowski et al. ........... 260/239 BD |

FOREIGN PATENT DOCUMENTS 2221558 11/1973 Fed. Rep. of Germany ... 260/239 BD

OTHER PUBLICATIONS

McOmie, Advances in Organic Chemistry: Methods and Results, vol. 3, (Interscience, New York, 1963), pp. 219-221.

Wünsch et al., Ber. Deut. Chem., vol. 102, pp. 3891-3902, (1969).
Field et al., J. Org. Chem., vol. 30, pp. 2098-2102, (1965).
Zioaudrou et al., J. Am. Chem. Soc., vol. 85, pp. 3258-3264.

*Primary Examiner*—Alton D. Rollins
*Attorney, Agent, or Firm*—Michael J. Striker

[57] ABSTRACT

1,2,3,4-Tetrahydro-1,5-benzodiazocines having the following formula

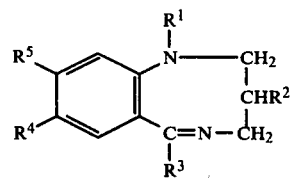

in which $R^1$ is a hydrogen, alkyl radical having at most 6 carbon atoms, methoxyethyl, or benzyl radical, $R^2$ is a halo, hydroxyl, acetoxy or benzoxy radical, $R^3$ is a phenyl, 2-methylphenyl, 2-chlorophenyl, 2-bromophenyl, 2-fluorophenyl, 2-nitrophenyl, 2-(trifluoromethyl)phenyl, 3-(trifluoromethyl)phenyl, 2,3-dichlorophenyl, 2,4-dichlorophenyl, 2,6-dichlorophenyl, 3,4-dichlorophenyl, 3,4-dimethoxyphenyl, or 3,4,5-trimethoxyphenyl radical, $R^4$ is a hydrogen, chloro, fluoro, bromo, trifluoromethyl, methyl, methoxy, or methylthio radical, and $R^5$ is a hydrogen or methoxy radical, or $R^4$ and $R^5$ together are an ethylendioxy radical, or an acid addition salt of the said benzodiazocine, and processes of making the same are described. The benzodiazocines are tranquilizing agents and starting compounds for the production of benzodiazepines which are also useful as tranquilizing agents as well as anticonvulsive, sedative, and muscle-relaxing agents.

19 Claims, No Drawings

BENDODIAZOCINE DERIVATIVES AND PROCESS OF MAKING THE SAME

CROSS-REFERENCE TO RELATED APPLICATIONS

This application is a continuation of our prior application Ser. No. 588,969, filed June 20, 1975, now abandoned, which is a continuation-in-part of our applications (1) Ser. No. 355,987, filed May 1, 1973, now abandoned, (2) Ser. No. 355,986, filed May 1, 1973, now U.S. Pat. No. 3,998,809, and (3) Ser. No. 355,989, filed May 1, 1973, now abandoned in favor of continuation-in-part application Ser. No. 598,880, filed July 24, 1975.

Specification Ser. No. 588,969 and the prior application Ser. No. 355,987, both now abandoned, cover the same subject matter as the present specification, e.g. the benzodiazocine derivatives and a process for making them. There is also disclosed a process for the production of acyldiamines, the starting products for making the benzodiazocines.

This process for making acyldiamines and additionally numerous other acyldiamines are described in the related application Ser. No. 355,986, now U.S. Pat. No. 3,998,809.

SUMMARY OF THE INVENTION

The present invention pertains to new benzodiazocines having the formula:

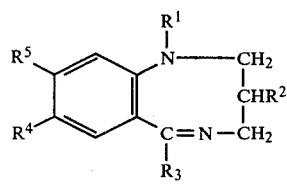

in which $R^1$ is a hydrogen, methoxyethyl, benzyl or alkyl radical having at most 6 carbon atoms, $R^2$ is a halo, hydroxyl, acetoxy or benzoxy radical, $R^3$ is a phenyl, 2-methylphenyl, 2-chlorophenyl, 2-bromophenyl, 2-fluorophenyl, 2-nitrophenyl, 2-(trifluoromethyl)phenyl, 3-(trifluoromethyl)phenyl, 2,3-dichlorophenyl, 2,4-dichlorophenyl, 2,6-dichlorophenyl, 3,4-dichlorophenyl, 3,4-dimethoxyphenyl, or 3,4,5-trimethoxyphenyl radical, $R^4$ is a hydrogen, chloro, fluoro, bromo, trifluoromethyl, methyl, methoxy, or methylthio radical, $R^5$ is a hydrogen or methoxy radical, or $R^4$ and $R^5$ together are an ethylendioxy radical or an acid addition salt of the said benzodiazocine which benzodiazocines are useful tranquilizing agents that is, antineurotic and antianxiety agents.

Alkyl radicals having at most 6 carbon atoms that are included in the foregoing definition of $R^1$ are methyl, ethyl, propyl, isopropyl and all isomeric butyl, pentyl and hexyl radicals.

Preferred halo radicals that are included in the foregoing definition of $R^2$ are chloro and bromo radicals.

The benzodiazocines of the present invention can be made in an inert solvent by heating an acyldiamine having the following formula:

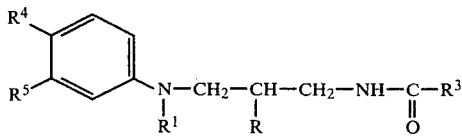

in which $R^1$, $R^3$, $R^4$ and $R^5$ have the same significance as in the foregoing formula I and R is a hydroxyl, acetoxy or benzoxy radical, with a phosphorus oxyhalide.

The foregoing acyldiamines which are required for the preparation of the benzodiazocines of the present invention are themselves novel compounds which can in turn be made starting from known diamines having the following formula:

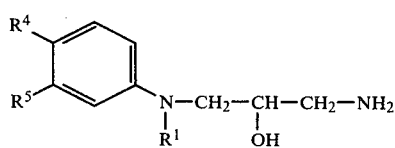

in which $R^1$, $R^4$ and $R^5$ have the same significance as in the foregoing formulae I and II. The preparation of the said starting acyldiamines is described hereinafter in connection with the detailed description.

DETAILED DESCRIPTION AND PREFERRED EMBODIMENTS OF THE INVENTION

The benzodiazocines of the present invention can be made by heating, at an elevated temperature in an inert solvent, an acyldiamine having the formula

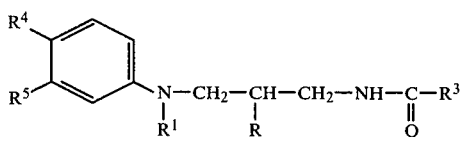

in which $R^1$, $R^3$, $R^4$ and $R^5$ have the same significance as hereinbefore and R is a hydroxyl, acetoxy or benzoxy radical, with a phosphorus oxyhalide, preferably phosphorus oxychloride or phosphorus oxybromide. The benzodiazocines that are thus obtained have the following formula

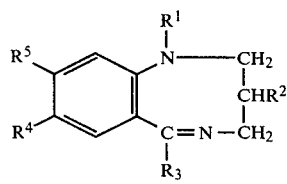

in which $R^1$, $R^3$, $R^4$ and $R^5$ have the same significance as hereinbefore and $R^2$ is a halo, acetoxy or benzoxy radical. The hydroxyl radical of acyldiamines having the foregoing formula II in which R is a hydroxyl radical is converted when the acyldiamine is heated with the phosphorus oxyhalide into a halo radical; the acetoxy or benzoxy radicals of acyldiamines having the formula II in which R is an acetoxy or benzoxy radical are not affected by similar heating with the phosphorus oxyhalide. To prevent the formation of by-products when an acyldiamine in which R is hydroxyl is cyclized with the phosphorus oxyhalide cyclization agent, the acyldiamine can first be converted to a corresponding acyldiamine in which R is acetoxy or benzoxy.

A benzodiazocine in which the $R^2$ of formula I is the hydroxyl radical can then be obtained by hydrolyzing the corresponding benzodiazocine in which the $R^2$ radical is the acetoxy or benzoxy radical in the presence of an alkali-metal hydroxide such as potassium hydroxide or sodium hydroxide.

The conversion of the acyldiamine to the corresponding benzodiazocine by ring closure or cyclization must be carried out under suitable conditions. The preferred cyclization agent for converting an acyldiamine in which R is a hydroxyl radical to a benzodiazocine is phosphorus oxychloride.

Inert solvents that can be used are nitrobenzene, 1,1,2,2-tetrachloroethane or the phosphorus oxyhalide cyclization agent itself.

The reaction temperature that is used depends upon the specific $R^3$, $R^4$ and $R^5$ radicals of the acyldiamine but preferably is between 50° and 100° C. when the R radical of the acyldiamine is a hydroxyl radical. For example, a lower reaction temperature can be used if the $R^5$ radical of the acyldiamine is an alkoxy radical then would be used when the $R^5$ radical is a hydrogen radical. In such cases, higher temperatures such as temperature above 100° C. favor the formation of benzodiazepines having the formula

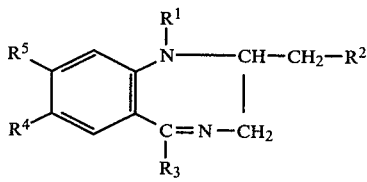

in which $R^1$, $R^3$, $R^4$ and $R^5$ have the same significance as hereinbefore specified, as described in application Ser. No. 355,986, filed May 1, 1973, now U.S. Pat. No. 3,998,809 and $R^2$ is a halo radical.

Reaction temperatures within a broader range between 50° and 150° C., and preferably between 110° and 130° C., can be used when the R radical of the acyldiamine that is heated with the phosphorus oxyhalide is an acetoxy or benzoxy radical, in which case the $R^3$ radical of the resulting benzodiazocine will be the acetoxy or benzoxy radical that can then be converted to the hydroxyl radical by conventional hydrolysis with water in the presence of an alkali-metal hydroxide, as described hereinbefore.

The conversion of acyldiamines, specifically N-phenyl-N'-benzoyl-2-hydroxypropylenediamines, by an intramolecular cyclization of the type of the Bischler-Napieralski reaction [Berichte, vol. 26, page 1903 (1893)] to produce a 1,2,3,4-tetrahydro-1,5-benzodiazocine containing an 8-membered ring, as disclosed in this application, was quite unexpected, especially since the cyclization can be affected under such relatively mild conditions such as a relatively narrow temperature range in an inert solvent and in the presence of a phosphorus oxyhalide and within a relatively short period of time to produce a high yield of the desired benzodiazocine.

The preparation of 7-membered ring compounds by cyclization of N-phenyl-N-benzoylethylenediamine with a phosphorus oxyhalide has heretofore been disclosed in U.S. Pat. No. 3,501,460. The resulting compounds, however, are 2,3-dihydro-1H-1,4-benzodiazepines that lack a substituent in the 2-position while such substituents as are present in the compounds obtained from the present benzodiazocines as further disclosed in our application Ser. No. 355,989, filed May 1, 1973 abandoned, now Ser. No. 598,880, filed July 24, 1975.

The invention is further described in connection with the Examples which follow which were selected solely for purposes of illustration and consequently are not to be construed as restrictive of the invention or its scope.

EXAMPLE 1

A mixture of 61 grams of N-methyl-N-(2-benzoxy-3-benzoylaminopropyl)-4-chloroaniline prepared as described hereinafter in Example B and 60 milliliters of phosphorus oxychloride was heated at a temperature of 120° C. for a period of 16 hours. The reaction product was then poured onto ice and an aqueous solution of sodium hydroxide was then slowly added thereto with stirring until the mixture was alkaline. The resulting solution was then extracted with chloroform and the chloroform extract was concentrated by evaporation at a subatmospheric pressure and the residue was recrystallized from acetone. There was thus obtained 8-chloro-1-methyl-3-benzoxy-6-phenyl-1,2,3,4-tetrahydro-1,5-benzodiazocine having a melting point of 179°–180° C.

EXAMPLE 2

A solution of 5.9 grams of the benzodiazocine produced in Example 1 in 200 milliliters of dioxane containing 50 milliliters of a 5% aqueous sodium hydroxide solution was heated under gentle reflux for 20 minutes. The dioxane was then distilled therefrom at a subatmospheric pressure and the aqueous solution that remained was extracted several times with chloroform and the chloroform extracts were then combined and concentrated by evaporation at a subatmospheric pressure and the residue was recrystallized from diethyl ether. There was thus obtained 8-chloro-1-methyl-3-hydroxy-6-phenyl-1,2,3,4-tetrahydro-1,5-benzodiazocine having a melting point of 169°–170° C.

EXAMPLE 3

A mixture of 32 grams of N-methyl-N-(2-hydroxy-3-benzoylaminopropyl)-4-chloroaniline and 50 milliliters of phosphorus oxychloride and 100 milliliters of nitrobenzene was heated at a temperature of 95° C. during the course of 22 hours. The excess phosphorus oxychloride and the nitrobenzene were then distilled therefrom at a subatmospheric pressure. The residue was then extracted with chloroform and treated with ice water and dilute sodium hydroxide as described hereinbefore in Example 1. The chloroform extract was then concentrated by evaporation at a subatmospheric pressure. The residue was dissolved in diethyl ether and an isopropanol solution of hydrogen chloride was then added thereto. After recrystallization from a mixture of ethanol and diethyl ether there was obtained 3,8-dichloro-1-methyl-6-phenyl-1,2,3,4-tetrahydro-1,5-benzodiazocine hydrochloride having a melting point of 195°–196° C.

The following compounds were produced in accordance with the same general procedures that were described hereinbefore in Examples 1 to 3:

1-Methyl-3-acetoxy-6-phenyl-1,2,3,4-tetrahydro-1,5-benzodiazocine (oil)

1-Methyl-3-hydroxy-6-phenyl-1,2,3,4-tetrahydro-1,5-benzodiazocine, maleate thereof had a m.p. of 135°–137° C.

1-Methyl-3-acetoxy-6-(3,4,5-trimethoxyphenyl)-1,2,3,4-tetrahydro-1,5-benzodiazocine, m.p. 191°–192° C.

1-Methyl-3-benzoxy-6-phenyl-1,2,3,4-tetrahydro-1,5-benzodiazocine, m.p. 192°–194° C.

8-Chloro-1-methyl-3-hydroxy-6-(2-chlorophenyl)-1,2,3,4-tetrahydro-1,5-benzodiazocine, hydrochloride thereof had a m.p. of 180°–184° C.

1-Methyl-3-chloro-6-(2-chlorophenyl)-1,2,3,4-tetrahydro-1,5-benzodiazocine, m.p. 135°–136° C.

3,8-Dichloro-1-methyl-6-(2-chlorophenyl)-1,2,3,4-tetrahydro-1,5-benzodiazocine, hydrochloride thereof had a m.p. of 166°–169° C.

1-Methyl-3-hydroxy-8-bromo-6-(2-chlorophenyl)-1,2,3,4-tetrahydro-1,5-benzodiazocine, m.p. 189°–190° C.

1-Methyl-3-acetoxy-6-(2-chlorophenyl)-1,2,3,4-tetrahydro-1,5-benzodiazocine (oil)

1-Methyl-3-chloro-8-bromo-6-(2-chlorophenyl)-1,2,3,4-tetrahydro-1,5-benzodiazocine, m.p. 129°–131° C.

The following compounds can likewise be prepared by the same general procedures that were described hereinbefore in Examples 1 to 3:

1-Methyl-3-chloro-6-(3,4-dimethoxyphenyl)-8,9-dimethoxy-1,2,3,4-tetrahydro-1,5-benzodiazocine 1-Methyl-3-chloro-6-(3,4-dimethoxyphenyl)8,9-ethylenedioxy-1,2,3,4-tetrahydro-1,5-benzodiazocine 1-Methyl-3-chloro-6-(phenyl)-8,9-ethylenedioxy-1,2,3,4-tetrahydro-1,5-benzodiazocine 1-Methyl-3-chloro-6-(2-chlorophenyl)-8-methylthio-1,2,3,4-tetrahydro-1,5-benzodiazocine 1-Methyl-3,8-dichloro-6-(2,6-dichlorophenyl)-1,2,3,4-tetrahydro-1,5-benzodiazocine 1-Methyl-3,8-dichloro-6-(2,3-dichlorophenyl)-1,2,3,4-tetrahydro-1,5-benzodiazocine 1-Methyl-3,8-dichloro-6-(2-methylphenyl)-1,2,3,4-tetrahydro-1,5-benzodiazocine 1-Methyl-3,8-dichloro-6-(2-bromophenyl)-1,2,3,4-tetrahydro-1,5-benzodiazocine 1-Ethyl-3,8-dichloro-6-phenyl-1,2,3,4-tetrahydro-1,5-benzodiazocine 1-(2-Methoxyethyl)-3,8-dichloro-6-phenyl-1,2,3,4-tetrahydro-1,5-benzodiazocine 1-Methyl-3,8-dichloro-6-(2-fluorophenyl)-1,5-benzodiazocine 1-Methyl-3-chloro-6-(3,4,5-trimethoxyphenyl)-1,2,3,4-tetrahydro-1,5-benzodiazocine 1-Methyl-3-chloro-6-phenyl-8-fluoro-1,2,3,4-tetrahydro-1,5-benzodiazocine 1-Methyl-3-chloro-6-phenyl-1,2,3,4-tetrahydro-1,5-benzodiazocine 1-Methyl-3-acetoxy-6-(2-fluorophenyl)-8-chloro-1,2,3,4-tetrahydro-1,5-benzodiazocine 1-Methyl-3,8-dichloro-6-(2-trifluoromethylphenyl)-1,2,3,4-tetrahydro-1,5-benzodiazocine 1-Methyl-3,8-dichloro-6-(3,4-dimethoxyphenyl)-1,2,3,4-tetrahydro-1,5-benzodiazocine 1-Methyl-3,8-dichloro-6-(3,4-dichlorophenyl)-1,2,3,4-tetrahydro-1,5-benzodiazocine 1-Methyl-3-chloro-6-phenyl-8-methoxy-1,2,3,4-tetrahydro-1,5-benzodiazocine 1-Methyl-3,8-dichloro-6-(3-trifluoromethylphenyl)-1,2,3,4-tetrahydro-1,5-benzodiazocine 1-Benzyl-3,8-dichloro-6-phenyl-1,2,3,4-tetrahydro-1,5-benzodiazocine.

Preparation of the Starting Acyldiamines:

To produce the acyldiamines having the formula II that are required to produce the benzodiazocines of the present invention, a diamine having the following formula

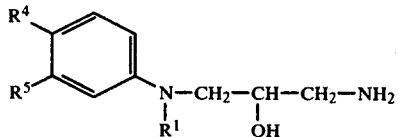

in which $R^1$, $R^4$ and $R^5$ have the same significance as hereinbefore, is reacted with a carboxylic acid or a derivative thereof that is capable of reacting with the diamine to form an acyldiamine. Such carboxylic acids and carboxylic acid derivatives such as carboxylic acid esters, carboxylic acid anhydrides and carboxylic acid halides have the following formulae

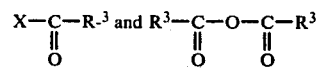

in which formulae $R^3$ has the same significance as in the foregoing formulae I and II, and X is a hydroxyl, halo or alkoxy radical.

The reaction of the diamine with the carboxylic acid or derivative thereof can be carried out in an inert solvent in the presence of an acid acceptor or acid-binding agent, preferred examples of which are tertiary amines such as triethylamine and pyridine. If the acid-binding agent is used in excess it can serve at the same time as the inert solvent in the reaction. The reaction can however also be carried out in an inert solvent in the absence of an acid-binding agent.

Suitable inert solvents for use for this purpose are for instance methylene chloride (dichloromethane) chloroform, acetone, dioxane, benzene, toluene and chlorobenzene.

The temperature at which the reaction is conducted depends on the particular carboxylic acid or derivative thereof and is between −30° C. and the boiling point of the solvent. The reaction can be carried out at an atmospheric or a superatmospheric pressure.

If equimolecular quantities of the diamine having the formula III and the carboxylic acid or derivative thereof are reacted, the principal product is an acyldiamine having the formula II hereinbefore in which R is a hydroxyl radical. The hydroxyl radical can then be esterified with acetic anhydride or benzoyl chloride or other suitable carboxylic acid anhydride, ester, or halide to produce the desired ester in which R is an acetoxy, benzoxy or similar radical. When 2 mols of benzoyl chloride, for example, are used for each mol of diamine, the product is an acyldiamine having the formula II hereinbefore in which R is the benzoxy radical.

The preparation of typical acyldiamines that are required for the production of the benzodiazocines of the present invention is illustrated in the following Examples.

EXAMPLE A

To a solution of 128 grams of N-methyl-N-(2-hydroxy-3-aminopropyl)-4-chloroaniline and 200 milliliters of chloroform containing 84 milliliters of triethylamine was slowly added with stirring 69.5 milliliters of benzoyl chloride. After 24 hours the chloroform solution was washed with water and dried over anhydrous sodium sulfate. The chloroform was then distilled off at a subatmospheric pressure and the crude product that was thus obtained was recrystallized from benzene. There was thus obtained 142.5 grams of N-methyl-N-(2-hydroxy-3-benzoylaminopropyl)-4-chloroaniline having a melting point of 136°–137° C. This product was used in Example 3 hereinbefore.

EXAMPLE B

To a solution of 59 grams of N-methyl-N-(2-hydroxy-3-aminopropyl)-4-chloroaniline in 1 liter of chloroform containing 85 milliliters of triethylamine was slowly added with stirring 70 milliliters of benzoyl chloride. The mixture was then heated under gentle reflux for a period of 4 hours and further treated as described hereinbefore in Example A. The crude product was recrystallized from isopropanol and there was thus obtained 61 grams of N-methyl-N-(2-benzoxy-3-benzoylaminopropyl)-4-chloroaniline having a melting point of 145°–148° C. This product was used in Example 1 hereinbefore.

EXAMPLE C

To a solution of 45.4 grams of N-methyl-N-[2-hydroxy-3-(3,4,5-trimethoxybenzoyl)aminopropyl]aniline in 250 milliliters of pyridine was slowly added with stirring 250 milliliters of acetic anhydride. After 48 hours the solution was poured into water and extracted with chloroform. The chloroform extract was concentrated by evaporation at a subatmospheric pressure and the residue was recrystallized from diethyl ether. There was thus obtained N-methyl-N-[2-acetoxy-3-(3,4,5-trimethoxybenzoyl)aminopropyl]aniline having a melting point of 90°–92° C.

This acyldiamine was used to prepare 1-methyl-3-acetoxy-6-(3,4,5-trimethoxyphenyl)-1,2,3,4-tetrahydro-1,5-benzodiazocine having a melting point of 191°–192° C.

The following compounds were prepared by exactly the same general procedures that were hereinbefore described and illustrated in Examples A to C:

N-Methyl-N-[2-hydroxy-3-(3,4-dimethoxybenzoyl)-aminopropyl]-3,4-dimethoxyaniline (oil)
N-Methyl-N-[2-hydroxy-3-(3,4-dimethoxybenzoyl)-aminopropyl]-3,4-(ethylenedioxy)aniline (oil)
N-Methyl-N-[2-hydroxy-3-(2-chlorobenzoyl)-aminopropyl]-3,4-(ethylenedioxy)aniline, m.p. 105°–107° C.
N-Methyl-N-(2-hydroxy-3-benzoylaminopropyl)-4-methyl-thioaniline, m.p. 141°–142° C.
N-Methyl-N-[2-hydroxy-3-(2,6-dichlorobenzoyl)-aminopropyl]-4-chloroaniline (oil)
N-Methyl-N-[2-hydroxy-3-(2,3-dichlorobenzoyl)-aminopropyl]-4-chloroaniline m.p. 91°–95° C.
N-Methyl-N-[2-hydroxy-3-(2-methylbenzoyl)-aminopropyl]-4-chloroaniline, m.p. 108°–113° C.
N-Methyl-N-[2-hydroxy-3-(2-bromobenzoyl)-aminopropyl]-4-chloroaniline, m.p. 118°–123° C.
N-Methyl-N-[2-hydroxy-3-(2-nitrobenzoyl)-aminopropyl]-4-chloroaniline, m.p. 132°–133° C.
N-Ethyl-N-(2-hydroxy-3-benzoylaminopropyl)-4-chloroaniline, m.p. 121°–123° C.
N-$\beta$-Methoxyethyl-N-(2-hydroxy-3-benzoylaminopropyl)-4-chloroaniline, m.p. 120°–122° C.
N-Methyl-N-[2-hydroxy-3-(3,4,5-trimethoxybenzoyl)-aminopropyl]aniline, m.p. 126°–129° C.
N-Methyl-N-(2-hydroxy-3-benzoylaminopropyl)-4-fluoroaniline, m.p. 115°–118° C.
N-Methyl-N-[2-hydroxy-3-(2-fluorobenzoyl)-aminopropyl]-4-chloroaniline, m.p. 105°–107° C.
N-Methyl-N-(2-hydroxy-3-benzoylaminopropyl)-aniline, m.p. 100°–103° C.
N-(2-Hydroxy-3-benzoylaminopropyl)-4-chloroaniline, m.p. 175°–177° C.
N-Methyl-N-(2-acetoxy-3-benzoylaminopropyl)-aniline (oil)
N-Methyl-N-[2-acetoxy-3-(2-fluorobenzoyl)-aminopropyl]-4'-chloroaniline (oil)
N-Methyl-N-[2-hydroxy-3-(2-chlorobenzoyl)-aminopropyl]-4-chloroaniline, m.p. 113°–115° C.
N-Methyl-N-[2-hydroxy-3-(2-trifluoromethylbenzoyl)-aminopropyl]-4-chloroaniline, m.p. 107°–109° C.
N-Methyl-N-[2-hydroxy-3-(3,4-dimethoxybenzoyl)-aminopropyl]-4-chloroaniline, m.p. 118°–121° C.
N-Methyl-N-[2-hydroxy-3-(3,4-dichlorobenzoyl)-aminopropyl]-4-chloroaniline, m.p. 115°–117° C.
N-Methyl-N-(2-benzoxy-3-benzoylaminopropyl)-aniline, m.p. 129°–130° C.
N-Methyl-N-[2-hydroxy-3-(2,4-dichlorobenzoyl)-aminopropyl]-4-chloroaniline, m.p. 98°–99° C.
N-Methyl-N-(2-hydroxy-3-benzoylaminopropyl)-4-methylaniline, m.p. 115° C.
N-Methyl-N-(2-hydroxy-3-benzoylaminopropyl)-4-methoxyaniline, m.p. 120° C.
N-Methyl-N-[2-hydroxy-3-(3-trifluoromethylbenzoyl)-aminopropyl]-4-chloroaniline (oil)
N-Benzyl-N-(2-hydroxy-3-benzoylaminopropyl)-4-chloroaniline, m.p. 128°–132° C.

Utility of the Compounds:

The benzodiazocines that are disclosed herein are useful starting compounds for preparation of the 2,3-dihydro-1H-1,4-benzodiazepines which are disclosed in our above-mentioned U.S. Pat. Ser. No. 3,998,809 and which are effective anticonvulsive, sedative, muscle-relaxing and tranquilizing agents.

The benzodiazocines that are disclosed herein are also useful tranquilizing agents, that is, as antineurotic and antianxiety agents.

8-Chloro-1-methyl-3-hydroxy-6-(2-chlorophenyl)-1,2,3,4-tetrahydro-1,5-benzodiazocine was compared in several animal tests with meprobamate. The tests were as follows:

1. Acute toxicity: The acute toxicity was determined by a single oral administration to fasting white mice of the NMRI strain. The minimum lethal dose ($LD_{50}$) was computed in accordance with the method described by J. T. Litchfield and F. Wilcoxon in Journal of Pharmacology and Experimental Therapeutics, volume 96, page 99, (1949).

In this test, meprobamate had an acute toxicity ($LD_{50}$) of 1380 milligrams per kilogram of body weight, whereas the acute toxicity of the benzodiazocine was more than 1470 milligrams per kilogram of body weight.

2. Pentylenetetrazol spasm test: In this test the substances that were tested were administered orally to groups of six mice at doses differing from each other by the logarithm 0.1673. After 60 minutes, pentylenetetrazol was injected subcutaneously at a dosage of 100 milligrams per kilogram of body weight to the mice. The incidence of clonic and tonic spasms and death was observed during a period of 45 minutes and the animal was further observed for a total period of 3 hours. The protective effect against spasms and death was determined by comparison in simultaneous tests performed on control animals. The effective dose ($ED_{50}$) against spasm is determined from probability logarithmic dosage curves. In this test the effective dose ($ED_{50}$) of meprobamate was 81 milligrams per kilogram of body weight, whereas the effective dose of the benzodiazocine was 3.5 milligrams per kilogram of body weight.

Pharmaceutically acceptable acid addition salts of the benzodiazocines of the present invention can be made, for example, from acids such as acetic, propionic, diethylacetic, malonic, fumaric, maleic, lactic, tartaric, malic, citric, sulfuric, hydrochloric, hydrobromic and orthophosphoric acids. These acid salts can be used in place of the free bases themselves and have the advantage thereover of being soluble in water.

The benzodiazocines of the present invention can be used with the usual pharmaceutically acceptable diluents or carrier materials such as cellulose, starch, polyethylene glycol, magnesium stearate or talcum to produce compositions in unit-dosage forms. Water-soluble benzodiazocines can also be administered in the form of aqueous solutions.

The dosage that is administered is dependent upon the age, body weight and condition of the patient. Preferred doses are between 1 and 200 milligrams per day per kilogram of body weight. This amount may be administered as a single daily dose or may be distributed in smaller doses throughout the day. Normally smaller doses are used when the compounds are administered parenterally.

What is claimed as new and desired to be protected by Letters Patent is set forth in the appended claims.

1. A benzodiazocine having the formula

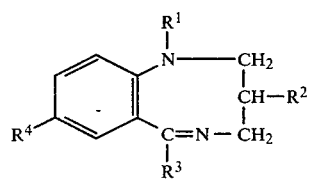

in which
 $R^1$ is methyl,
 $R^2$ is a hydroxy, chloro, acetoxy or benzoyloxy radical,
 $R^3$ is a phenyl, 2-chlorophenyl or 3,4,5-trimethoxyphenyl radical, and
 $R^4$ is a hydrogen or chloro radical.

2. The benzodiazocine of claim 1 wherein $R^2$ is benzoyloxy and $R^3$ is phenyl.

3. A benzodiazocine which is 8-chloro-1-methyl-3-benzoxy-6-phenyl-1,2,3,4-tetrahydro-1,5-benzodiazocine.

4. A benzodiazocine which is 8-chloro-1-methyl-3-hydroxy-6-phenyl-1,2,3,4-tetrahydro-1,5-benzodiazocine.

5. A benzodiazocine which is 3,8-dichloro-1-methyl-6-phenyl-1,2,3,4-tetrahydro-1,5-benzodiazocine.

6. A benzodiazocine which is 1-methyl-3-acetoxy-6-phenyl-1,2,3,4-tetrahydro-1,5-benzo-diazocine.

7. A benzodiazocine which is 1-methyl-3-hydroxy-6-phenyl-1,2,3,4-tetrahydro-1,5-benzodiazocine.

8. A benzodiazocine which is 1-methyl-3-acetoxy-6-(3,4,5-trimethoxyphenyl)-1,2,3,4-tetrahydro-1,5-benzodiazocine.

9. A benzodiazocine which is 1-methyl-3-benzoxy-6-phenyl-1,2,3,4-tetrahydro-1,5-benzodiazocine.

10. A benzodiazocine which is 8-chloro-1-methyl-3-hydroxy-6-(2-chlorophenyl)-1,2,3,4-tetrahydro-1,5-benzodiazocine.

11. A benzodiazocine which is 1-methyl-3-chloro-6-(2-chlorophenyl)-1,2,3,4-tetrahydro-1,5-benzodiazocine.

12. A benzodiazocine which is 3,8-dichloro-1-methyl-6-(2-chlorophenyl)-1,2,3,4-tetrahydro-1,5-benzodiazocine.

13. A process for the production of a benzodiazocine as defined in claim 1 in which the $R^2$ radical is chloro, and $R^1$, $R^3$ and $R^4$ have the same meaning as in claim 20, which process comprises heating an acyldiamine having the formula

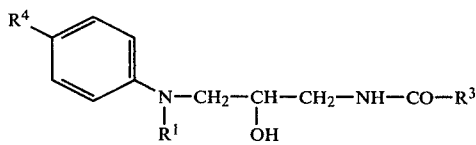

in which $R^1$, $R^3$ and $R^4$ have the same significance as before, with a phosphorus oxychloride in an inert solvent at a temperature between 50° and 100° C. and recovering the benzodiazocine which is chlorine substituted in the 3-position.

14. The process as defined in claim 13 in which the inert solvent is nitrobenzene or 1,1,2,2-tetrachloroethane.

15. A process for the production of a benzodiazocine having the formula

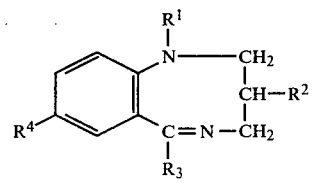

in which
 $R_1$ is methyl,
 $R_2$ is an acetoxy or benzoxy radical,
 $R_3$ is a phenyl, 2-chlorophenyl, or 3,4,5-Trimethoxyphenyl radical, and
 $R_4$ is a hydrogen or chloro radical, which process comprises heating an acyldiamine having the formula

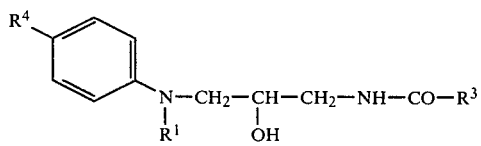

in which R is acetoxy or benzoxy and $R^1$, $R^3$ and $R^4$ have the same significance as before, with a phosphorus oxyhalide in an inert solvent at a temperature between 50° and 150° C. and recovering said benzodiazocine.

16. The process of claim 15 in which the inert solvent is nitrobenzene or 1,1,2,2-tetrachloroethane.

17. The process of claim 15 wherein the phosphorus oxyhalide is phosphorus oxychloride.

18. The process of claim 15 followed by the step of hydrolyzing the obtained benzodiazocine in which $R^2$ is acetoxy or benzoxy in the presence of an alkali metal hydroxide so as to obtain the corresponding benzodiazocine in which $R^2$ is hydroxy.

19. The process of claim 18 wherein the said temperature is between 110° and 130° C.

* * * * *